(12) United States Patent
Porsö et al.

(10) Patent No.: US 6,974,890 B1
(45) Date of Patent: Dec. 13, 2005

(54) ABSORBENT STRUCTURE IN AN ABSORBENT ARTICLE, COMPRISING A PARTIALLY NEUTRALIZED SUPERABSORBENT MATERIAL AND AN ABSORBENT ARTICLE THAT COMPRISES THE ABSORBENT STRUCTURE

(75) Inventors: Berith Porsö, Partille (SE); Ulrika Hagrud, Göteborg (SE); Marie-Louise Lagerstedt Eidrup, Guildford (GB); Jan Hansson, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/857,374

(22) PCT Filed: Dec. 15, 1999

(86) PCT No.: PCT/SE99/02371

§ 371 (c)(1),
(2), (4) Date: Aug. 2, 2001

(87) PCT Pub. No.: WO00/35505

PCT Pub. Date: Jun. 22, 2000

(30) Foreign Application Priority Data

Dec. 16, 1998 (SE) .................................... 9804361

(51) Int. Cl.[7] ............................................. A61F 13/15
(52) U.S. Cl. ..................... 604/368; 604/374; 604/378
(58) Field of Search .............................. 604/368, 374, 604/378

(56) References Cited

U.S. PATENT DOCUMENTS

| 4,657,537 | A | | 4/1987 | Zimmerer |
| 4,685,909 | A | * | 8/1987 | Berg et al. .................. 604/360 |
| 5,041,496 | A | | 8/1991 | Engelhardt et al. |
| 5,599,335 | A | * | 2/1997 | Goldman et al. ........... 604/368 |
| 5,827,255 | A | * | 10/1998 | Crainic ....................... 604/378 |
| 5,836,929 | A | * | 11/1998 | Bewick-Sonntag et al. . 604/368 |
| 5,977,014 | A | * | 11/1999 | Plischke et al. ............ 502/401 |
| 5,994,614 | A | * | 11/1999 | Wada et al. ................ 604/378 |
| 6,194,631 | B1 | * | 2/2001 | Mitchell et al. ............ 604/368 |
| 6,222,091 | B1 | * | 4/2001 | Beihoffer et al. .......... 604/368 |

FOREIGN PATENT DOCUMENTS

| EP | 339461 | 11/1989 |
| EP | 532002 | 3/1993 |
| SE | 511838 | 12/1999 |
| WO | 95/99183 | 1/1995 |

* cited by examiner

Primary Examiner—Larry I. Schwartz
Assistant Examiner—C. Lynne Anderson
(74) Attorney, Agent, or Firm—Buchanan Ingersoll PC

(57) ABSTRACT

An absorbent structure for absorbent articles such as diapers, incontinence protectors, sanitary napkins, panty liners and like articles, the absorbent structure comprising at least 40 percent by weight superabsorbent material, based on the total weight of the absorbent structure in a dry state in the region or regions in which the superabsorbent is distributed, wherein the superabsorbent material is only partially neutralized. Absorbent articles that include the absorbent structure.

13 Claims, 1 Drawing Sheet

ABSORBENT STRUCTURE IN AN ABSORBENT ARTICLE, COMPRISING A PARTIALLY NEUTRALIZED SUPERABSORBENT MATERIAL AND AN ABSORBENT ARTICLE THAT COMPRISES THE ABSORBENT STRUCTURE

The present invention relates to an absorbent structure in an absorbent article, such as a diaper, a pant diaper, an incontinence protector, a sanitary napkin, a panty liner or some like article, that comprises a partially neutralised superabsorbent material, and also relates to an absorbent article that comprises said absorbent structure.

BACKGROUND

An absorbent article normally comprises an upper liquid-permeable sheet, an absorbent sheet, and a bottom liquid-impermeable barrier sheet, said sheets being delimited by two transverse edges and two longitudinal edges. The article includes a front part and a rear part between which there extends a crotch part that has a wetting region within which the major part of the body fluid is delivered. The absorbent sheet, or layer, will often include a superabsorbent material.

The superabsorbent material is present in particle form, e.g. in a grain, granule, flake or fibre form, and is mixed or layered with other absorbent material, normally cellulose fibres. Superabsorbent materials are polymers that are able to absorb such liquid as water and body fluids, e.g. urine and blood, while swelling and forming a gel that will not dissolve in water. Some superabsorbent materials are able to retain absorbed liquid even when subjected to external pressures. These materials have been used widely in absorbent sanitary products, such as diapers, sanitary napkins, incontinence protectors and like products.

The effectiveness of a superabsorbent material is contingent on many factors, such as how it is mixed into the absorbent structure, its particle form and particle size, and also its physical and chemical properties such as absorption rate, gel strength and liquid retention properties. The absorption capacity of a superabsorbent can be influenced negatively by a phenomenon known as gel blocking. Gel blocking is when the superabsorbent material forms a gel that blocks the pores in the fibre structure or the particle interstices when the absorbent article is wetted. Such blocking impedes the transportation of liquid from the wetted area out to the remainder of the absorbent body and will prevent the total absorption capacity of the absorbent body from being fully utilised and also creates a leakage risk.

With the intention of abating the problem caused by gel blocking, it is known, e.g., to use superabsorbent particles that are embraced by a casing which is only slowly dissolved in and/or penetrated by the liquid to be absorbed, such as to impart to the superabsorbent material a delayed activation time. Prior publication WO 95/00183 teaches an absorbent article that has an absorbent structure which includes superabsorbent material having a delayed activation time in the wetting region of the structure, and conventional superabsorbent material in those regions that lie outside this wetting region.

The problem of gel blocking can also be reduced by using a superabsorbent material that has a high gel strength. High gel strength superabsorbent materials are able to retain absorbed liquid when the swollen material is subjected to external loads, and is also able to absorb a significant quantity of liquid when subjected to external loads. EP 0 339 461 describes a high gel strength superabsorbent for use in absorbent articles. This superabsorbent is able to retain its form to a large extent and will not collapse when swelling.

EP 0 532 002 teaches a superabsorbent material of high gel strength that also has a certain liquid dispersion capacity.

Thus, as described above, one problem with absorbent articles that include superabsorbent material is gel blocking. This increases the risk of leakage and prevents the total capacity of the absorbent structure from being fully utilised. Another drawback with conventional superabsorbents is found in the large extent to which they swell. High concentrations of superabsorbent can swell into a large clump at the wetting point, so as to cause discomfort to the wearer after wetting the article.

The object of the present invention is to provide a solution to these problems.

SUMMARY OF THE INVENTION

The invention relates to an absorbent structure that comprises solely partially neutralised superabsorbent material that does not swell to the same extent as conventional superabsorbent material and therewith allows higher superabsorbent concentrations to be used. When compared with conventional superabsorbent materials, the partially neutralised superabsorbent material absorbs liquid more slowly and therewith enables the liquid to disperse to a greater extent before it swells. Conventional superabsorbent material has a degree of neutralisation of about 70%.

The present invention relates to an absorbent structure in absorbent articles, such as diapers, pant diapers, incontinence protectors, sanitary napkins, panty liners and like articles, wherein the structure comprises at least 40 percent by weight superabsorbent material, based on the total weight of said structure in a dry state in the region or regions in which the superabsorbent material is distributed, said superabsorbent material having a degree of neutralisation of between 20 and 50%.

The invention also relates to an absorbent article that includes the absorbent structure.

One advantage afforded by the present invention is that an absorbent article can be given a thinness which allows the inventive article to be worn comfortably and discretely. Another advantage afforded by the partially neutralised superabsorbent is that it prevents the occurrence of malodours and skin irritation when the absorbent article is worn.

DESCRIPTION OF THE INVENTION

Figure 1:
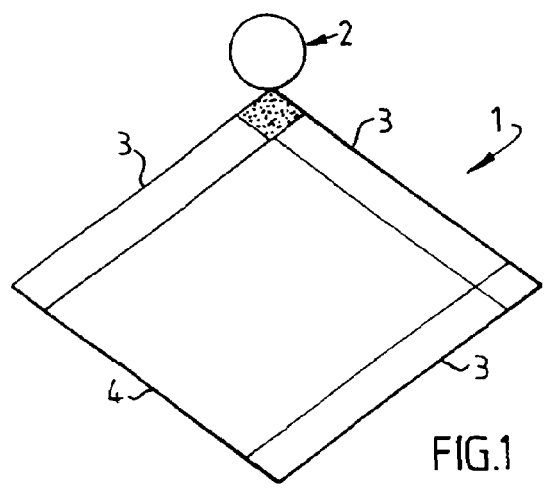
FIG. 1 illustrates a bag used in tests in Example 1.

The invention relates to an absorbent structure that comprises partially neutralised superabsorbent material. The aforesaid problems are therewith solved, by virtue of the fact that a partially neutralised superabsorbent material will not swell to the same extent as a conventional superabsorbent material, i.e. a superabsorbent material that has a degree of neutralisation of about 70%, and will absorb liquid more slowly than said conventional superabsorbent.

A cross-linked polyacrylate of the kind described in European Patent Specification EP 0 391 108, Casella AG, is an example of one suitable partially neutralised superabsorbent material that can be used in accordance with the invention.

A superabsorbent of this kind does not swell to the same extent as a superabsorbent material that has a higher degree of neutralisation, meaning that the superabsorbent will take up less volume in a swollen state. Consequently, there is less risk that the superabsorbent material when swollen will prevent the transportation of liquid through the pore structure that surrounds the superabsorbent material/the superabsorbent particles. A partially neutralised superabsorbent material according to the invention will, moreover, absorb liquid more slowly than a superabsorbent material that has a higher degree of neutralisation. This slower absorption rate of the partially neutralised superabsorbent enables a larger volume of liquid to disperse from the wetting point to other parts of the absorbent structure and therewith enables the total absorption capacity of the article to be utilised to a greater extent. The examples given below show that the partially neutralised superabsorbent material according to the invention absorbs liquid more slowly and in smaller volumes than conventional superabsorbent materials.

The superabsorbent is comprised of cross-linked polymerised acrylic acid. An ion complex of $COO^-$ and $Na^+$ or K is formed in the neutralisation process. As liquid is absorbed, an ion exchange takes place between $Na^+$ and other ions. The partially neutralised superabsorbent contains fewer ions ($COO^-$) than the conventional superabsorbent. The ions ($COO^-$) are available for liquid absorption and the fact that fewer ions ($COO^-$) are available means that the partially neutralised superabsorbent has a somewhat lower absorption capacity. A large number of carboxylic acid groups will be present, although these groups do not contribute towards absorption but impart to the superabsorbent a pH which is lower than that of a conventional superabsorbent.

Because the superabsorbent used in accordance with the invention absorbs smaller volumes of liquid, the article can be given a higher concentration of superabsorbent without becoming uncomfortable to wear after being wetted. According to the invention, with respect to the partially neutralised superabsorbent material, can now more than 40 percent by weight of superabsorbent material, calculated on the total dry weight of the absorbent structure, in that region or in those regions in which the superabsorbent material is distributed, be used without the aforedescribed problems occurring to the same high extent.

The aforesaid problems are thus solved by virtue of the superabsorbent being partially neutralised. The degree of neutralisation is 20 to 50% in comparison with a degree of neutralisation of about 70% in the case of a typical superabsorbent material.

As previously mentioned, the partially neutralised superabsorbent used in the absorbent structure in accordance with the invention has a lower absorption capacity and a slower liquid absorption rate than conventional superabsorbents. Because liquid is absorbed by the inventive superabsorbent more slowly, the liquid will have more time to disperse in the absorbent layer. The superabsorbent particles will therefore not impede the transportation of liquid to other parts of the absorbent structure to the same high extent. The lower absorption capacity of the superabsorbent also means that this dispersion function will remain active even over a long period of time. Neither will the superabsorbent particles swell to the same extent as conventional particles, therewith reducing the risk of lumps of superabsorbent being formed. A higher concentration of superabsorbent is permitted and more superabsorbent particles, which are small in size when swollen, can be accommodated in the same volume as fewer conventional superabsorbent particles, which are larger when swollen. This also contributes to a reduction in lump formations. A high concentration of partially neutralised superabsorbent material can thus be used in the absorbent structure, therewith resulting in an absorbent structure that has a high total absorption capacity and a high liquid dispersion capacity with retained comfort of the article after wetting.

There now follows a number of examples which show that the partially neutralised superabsorbent material according to the invention absorbs liquid at a slower rate and in smaller quantities than conventional superabsorbent material.

DESCRIPTION OF EXAMPLE 1

The following example is intended to illustrate that the partially neutralised superabsorbents used in the structure according to the invention absorb less liquid and at a slower rate than conventional superabsorbents. The tests were carried out by dip absorption intended for determining the absorption capacity of superabsorbents.

The Apparatus Used
  Polyester net, mesh size 59 $\mu$m
  Welding equipment
  Test liquid; see below
  Scales, accurate to 0.000 1 g Test Liquid
  Synthetic urine according to the following recipe:

|  | Concentration |
|---|---|
| Magnesium sulphate ($MgSO_4$) | 0.66 g/l |
| Potassium chloride (KCl) | 4.47 g/l |
| Sodium chloride (NaCl) | 7.60 g |
| Urea (Carbamide) ($NH_2CONH_2$) | 18.00 g/l |
| Potassium dihydrogen phosphate ($KH_2PO_4$) | 3.54 g/l |
| Sodium hydrogen phosphate ($Na_2HPO_4$) | 0.745 g/l |
| Triton X-100 0.1% | 1.00 g/l |
| Water de-ionised to 10% nykockin (colour) | 0.4 g/l |

Method
  The polyester net was clipped into pieces measuring 7×12 cm and the pieces then welded together along their edges to form bags.
  The bags were marked.
  The bags (P) were weighed to an accuracy of 0.0001 g.
  0.19–0.21 g of superabsorbent (S) was weighed into the bags at an accuracy of 0.0001 g.
  The superabsorbents were stirred.
  The bags were welded together and their weight checked.
    The superabsorbents were distributed uniformly in respective bags and the bags then placed carefully in the test liquid to soak.
  The bags were placed in the test liquid one at a time, so that the absorption time for each bag was precisely 15 seconds. The same degree of accuracy applies to the total absorption time up to 5 min., but not for 30 and 60 min.
  The bags were removed after 15 s. and hung up to drip for 2 min. The bags were hung from one corner so that the weld-free bottom of the bag faced downwards.
  See FIG. 1, which shows the bag 1 hanging from a ring 2 and comprising three welded edges 3 and a non-welded edge 4 which faces downwards.

Any droplets that formed on the bags were carefully wiped off.

The bags were weighed which gave $A_{(15s)}$, in other words the weight of the bag after 15 seconds measured to an accuracy of 0.0001 g.

The bags were placed in soak, taken up and allowed to drip after total absorption times of 30 sec., 45 sec., 1, 2, 5, 30 and 60 minutes, which gave $A_{(30s)}$, $A_{(45s)}$, $A_{(1\ m)}$, $A_{(2\ m)}$, $A_{(5\ m)}$, $A_{(30\ m)}$, $A_{(60\ m)}$.

The test liquid was changed after each completed test.

Calculations and Results Obtained $A_{(i)}$=Sample weight after absorption, g
i=15 s, 30 s, 45 s, 1 m, 2 m, 5 m,. 30 m, 60 m
P=Empty bag weight, g
S=Weight of superabsorbent, g
$D_{(i)}$=Sample absorption, g/g
K=Bag absorption correction
K=1.6 for i=15 s, 30 s, 45 s, 1, 2, 5, 30 and 60 min.

$$D(i) = \frac{A(i) - S - (P \times K)}{S}$$

Figure 2:
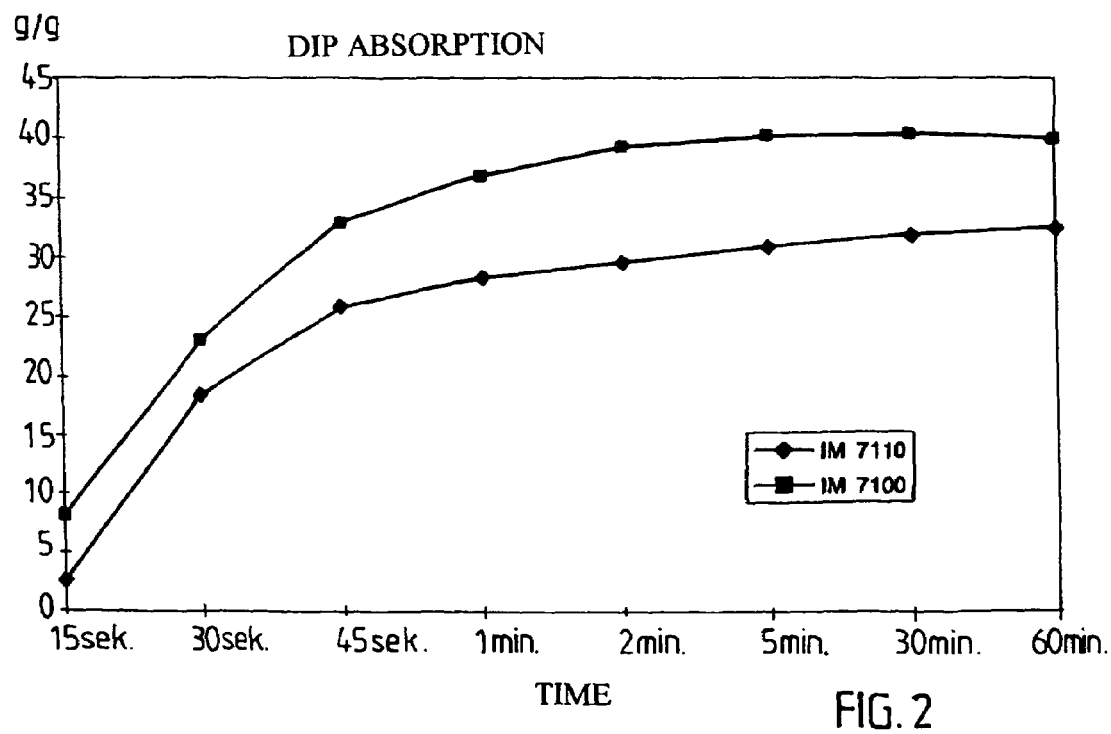
FIG. 2 illustrates results from Example 1 in the form of a curve where absorption is plotted against time.

The results are gathered in Table 1, where Hysorb C7110 (BASF) is the partially neutralised superabsorbent and Hysorb C7100 (BASF) is the conventional superabsorbent. It will be evident from the results that in the case of the partially neutralised superabsorbent Hysorb C7110 (BASF) absorption is at all times lower than the absorption of the conventional superabsorbent. The results are also shown in FIG. 2, where the, absorption D is plotted against time. The curve representing the partially neutralised superabsorbent constantly lies beneath the curve representing the conventional superabsorbent.

TABLE 1

| | Absorption (g/g) | |
| --- | --- | --- |
| TIME | Hysorb C7110 (BASF) | Hysorb C7100 (BASF) |
| 15 sec. | 2.4 | 8.0 |
| 30 sec. | 18.3 | 22.9 |
| 45 sec. | 25.9 | 32.9 |
| 1 min. | 28.4 | 36.9 |
| 2 min. | 29.6 | 39.3 |
| 5 min. | 30.9 | 40.3 |
| 30 min. | 32.0 | 40.5 |
| 60 min. | 32.8 | 40.1 |

All products that are worn in direct contact with the skin can lead to undesired side effects. These side effects can be the result of occlusion, the presence of moisture and factors of a mechanical, microbial and enzymatic nature, and can result in skin irritation, primary or secondary skin infections and undesired odours. An increase in pH is a normal occurrence when absorption products are worn against the skin. However, several undesired side effects can occur as a result of or in conjunction with an increase in pH. An example of such undesired side effects is Irritative contact dermatitis which has connection with the surface pH of the skin.

Another example of undesired side effects is that certain bacteria, such as Proteus, are able to metabolise the substances in urine and other body fluids and therewith give rise to malodorous substances, such as ammonia and amines, which also cause the pH to increase. The equilibrium of many odorous substances is displaced at high pH values so as to produce more volatile components and therefore become more odorous than at low pH values.

The growth of micro-organisms is also favoured by an environment such as that found in an absorbent article, where moisture, nutrients and heat are available among other things. High bacteria numbers constitute an infection risk. Furthermore, a high bacteria count also increases the risk of embarrassing malodours caused by the various substances that are formed by the biological or chemical degradation of body fluid constituents, such as the constituents of urine and menstrual fluid. The activity of micro-organisms is greatly dependent on pH and decreases with falling pH values.

The pH is lower when the absorbent structure includes partially neutralised superabsorbent material in accordance with the invention. The aforementioned undesired side effects are thus abated in an absorbent structure according to the invention.

Partially neutralised superabsorbent material is used in absorbent articles described in Swedish Patent Application SE 9702298-2. A reduction in pH value is achieved by virtue of the absorbent structure in the article including a pH-regulating substance in the form of a partially neutralised superabsorbent material. It has been observed that a pronounced inhibiting effect is obtained on undesired strains of micro-organisms and that the occurrence of undesired side effects that may result from wearing the article is reduced when the pH of the absorbent article after wetting lies in the range of 3.5–4.9.

Examples of the relationship between degree of neutralisation and the pH of the superabsorbent material will be evident from the following Table. The data included in the Table has been taken from SE 9702298-2.

| Degree of neutralisation % | pH |
| --- | --- |
| 18 | 4.0 |
| 25 | 4.3 |
| 30 | 4.5 |
| 35 | 4.7 |
| 45 | 5.0 |
| 60 | 5.5 |

The degree of neutralisation of the inventive superabsorbent material lies between 20 and 50%.

Another advantage afforded by the invention is that the occurrence of malodours and skin complaints that may arise from wearing an absorbent article in direct contact with the skin are avoided. The growth-inhibiting effect is based on the observation that the activity of many micro-organisms is greatly dependent on pH and diminishes with decreasing pH, and hence lowering of the pH value will result in diminished activity of the majority of micro-organisms. Enzymes, such as lipases and proteases, have an activity which is highly pH-dependent and which diminishes with decreasing pH values, and hence a lowering of pH values will also result in diminished enzyme activity and therewith a reduction in the negative skin influence of such activity.

The following examples illustrate the effect achieved in absorbent articles that have an absorbent body which comprises partially neutralised superabsorbent material, in comparison with conventional materials of a corresponding kind.

An absorbent body that contains absorbent material and absorbed liquid is, by nature, a heterogeneous system from a pH aspect. The system may include superabsorbent material, fibres and liquid that contains several types of ions. In order to obtain reproducible pH values, measurements must be taken at several places in the sample body and the mean value calculated on the basis thereof.

DESCRIPTION OF EXAMPLES 2, 3, 4 AND 5

Test Liquid

Sterile synthetic urine to which a micro-organism growth medium had been added. The synthetic urine contained monovalent and divalent cations and anions and urea and had been prepared in accordance with information set forth in Geigy, Scientific Tables, Vol. 2, 8th Ed., 1981, p. 53.

The micro-organism growth medium was based on information relating to Hook media and FSA media for enterobacteria. The mixture had a pH of 6.6.

Test Methods

Method 1, Manufacture of Absorbent Test Bodies

Absorbent bodies were produced with the aid of a slightly modified sample body former according to SCAN C 33:80. Fluff pulp and superabsorbent material of desired kind were weighed out, whereafter a uniform mixture of fluff pulp and superabsorbent material was passed in an air stream at a subpressure of about 85 mbar through a pipe having a diameter of 5 cm and provided with a bottom-carried metal net and thin tissue placed on said net. The fixture of fluff pulp and superabsorbent material was collected on the tissue disposed on the metal net and formed the absorbent body. The absorbent body was then weighed and compressed to a bulk density of 6–12 $cm^3/g$. A number of absorbent bodies designated Sample 1 and Sample 2 of mutually different compositions were then produced as described below. Sample 1 contained superabsorbents Hysorb C7110 (BASF), i.e. conventional superabsorbents, and Sample 2 contained partially neutralised superabsorbents Hysorb C7110 (BASF).

The absorbent bodies contained chemical cellulose pulp named Korsnäs EA.

The absorbent bodies had a total individual weight of 0.98 g.

The superabsorbent material weight 0.39 gram.

The chemical cellulose pulp weighed 0.59 gram.

Method 2, Measuring the pH of the Absorbent Body

An absorbent body having a diameter of about 50 mm was manufactured in accordance with Method 1. 14 ml of test liquid were added to an absorbent body, sample 1, and 11 ml of test liquid were added to another absorbent body, sample 2, and the absorbent bodies then allowed to swell for 30 min. (Different volumes of liquid were added since the amount of liquid absorbed by the superabsorbents varies.) The pH of respective absorbent bodies was then measured with the aid of a surface electrode, Flatbottnad Metrohm pH meter, Beckman Ø12 or Ø72. Parallel measurements were taken on at least two mutually different absorbent bodies. pH was measured at 10 points on each absorbent body and the mean value then calculated.

Method 3, Measuring Bacteria Inhibition in Absorbent Bodies

Bacteria suspensions of *Escherichia coli* (E.c.), *Proteus mirabilis* (P.m.), *Enterococcus faecalis* (E.f.) were cultivated in nutrient broth (Nutrient Broth Oxoid CMI) overnight at a temperature of 30° C. The graft cultures were diluted and the bacteria contents calculated. The cultures were mixed in different proportions, so that the final blend culture contained about $10^4$ organisms per ml synthetic urine. 10 ml of the synthetic urine were poured into a sterile sputum jar 70.5×52 mm, volume 100 ml, and the absorbent body was placed up-side-down in the jar and allowed to absorb liquid for 5 min., whereafter the jar was turned and incubated at 35° C. for 0, 6 and 12 hours respectively, whereafter the bacteria value in the absorbent body was determined. TGE agar was used as the nutrient for measuring the total number of bacteria while Drigalski agar was used for measuring specifically *Escherichia coli* and *Proteus mirabilis*, while Slanetz Bartley agar was used for specifically measuring *Enterococcus faecalis*. The results are shown in the tables below.

Test Results

EXAMPLE 2

It will be evident from Table 2 that the absorbent body according to Sample 2 comprising partially neutralised superabsorbents Hysorb C7110 (BASF) effectively inhibited the growth of Esherichia coli.

TABLE 2

| *Esherichia coli* | 0 hours | 6 hours | 12 hours |
| --- | --- | --- | --- |
| Sample 1 | 3.5 | 7.3 | 8.9 |
| Sample 2 | 3.5 | 3.7 | 3.3 |

EXAMPLE 3

It will be evident from Table 3 that the growth of *Proteus mirabilis* was effectively prohibited in Sample 2, which consisted of an absorbent body that included partially neutralised superabsorbents Hysorb C7110 (BASF).

TABLE 3

| *Proteus mirabilis* | 0 hours | 6 hours | 12 hours |
| --- | --- | --- | --- |
| Sample 1 | 3.2 | 6.3 | 9 |
| Sample 2 | 3.2 | <2 | <2 |

EXAMPLE 4

It will be evident from Table 4 that the growth of *Enterococcus faecalis* was effectively inhibited in Sample 2, which consisted of an absorbent body that included partially neutralised superabsorbents Hysorb C7110 (BASF).

TABLE 4

| *Enterococcus faecalis* | 0 hours | 6 hours | 12 hours |
| --- | --- | --- | --- |
| Sample 1 | 3.4 | 6.3 | 7.6 |
| Sample 2 | 3.4 | 3.3 | 3.4 |

The measurements in Examples 2–4 were made in accordance with Method 3.

It will be evident from Examples 2–4 that inhibition of micro-organism growth was good when using a partially neutralised superabsorbent in an absorbent body.

EXAMPLE 5

As will be evident from Table 5, the pH of an absorbent body consisting of Sample 1 that included conventional superabsorbent has a higher pH, above 6 and up to 8.7, after 12 hours. A lower pH of 4.6 is obtained in Sample 2 containing partially neutralised superabsorbent, thus a value which is suitable for inhibiting the growth of micro-organisms.

TABLE 5

| pH | 0 hours | 6 hours | 12 hours |
| --- | --- | --- | --- |
| Sample 1 | 6.1 | 6.2 | 8.7 |
| Sample 2 | 4.6 | 4.6 | 4.6 |

The measurements were made in accordance with Method 2.

The invention thus relates to an absorbent structure in absorbent articles, such as diapers, pants diapers, incontinence protectors, sanitary napkins, panty liners and like articles, wherein the structures comprises at least 40 percent by weight superabsorbent material based on the total weight of the absorbent structure in a dry state in the region or regions where the superabsorbent material is distributed, and wherein the superabsorbent material has a degree of neutralisation between 20 and 50%. A preferred degree of neutralisation is between 25 and 35%. At degrees of neutralisation between 20 and 50%, or between 25 and 35%, there is obtained a pH which is beneficial in counteracting the growth of micro-organisms for instance and in ablating undesired side effects. This also allows the article to be worn for a longer period of time, as a result of lowering the pH and also as a result of the higher absorption capacity of the inventive article. This longer use period afforded by the absorbent structure is highly beneficial coupled with the advantageous slower absorption rate and the lower total absorption of the individual superabsorbent particles, which reduces the risk of gel blocking and lump formations.

The amount of superabsorbent material present may lie between 40 and 50 percent by weight, based on the total weight of the absorbent structure in a dry state. The proportion of superabsorbent, however, may be higher, for instance up to 90 percent by weight. The absorbent structure may also be comprised solely of superabsorbent material.

The aforesaid proportion of superabsorbent material in the absorbent structure is primarily based on the total weight of the absorbent structure in a dry state in the region or regions in which the superabsorbent material is distributed.

Partially neutralised superabsorbent material is used chiefly in the absorbent structure according to the invention. However, the absorbent structure may also include conventional superabsorbent material. In this case, the partially neutralised superabsorbent may be placed in the wetting region while placing the conventional superabsorbent outside said wetting region. One advantage of localising the superabsorbent material that has the lowest degree of neutralisation in the wetting area of the article, i.e. in the crotch area of the article, and localising conventional superabsorbent material in the end parts of the article is that liquid dispersion is enhanced in such a structure from the wetting region to the end parts of said article. This enables the extent to which the total absorption capacity of the absorbent structure is utilised to be increased and also to reduce the danger of gel blocking in the wetting region.

Alternatively, superabsorbent distribution may be one in which the partially neutralised superabsorbent is placed in a first zone closer to the wearer, while the conventional superabsorbent is localised in a second zone which is located beneath the first zone as seen in a direction from the wearer of the absorbent article. This provides the same advantages as those mentioned above, because liquid will spread from the zone in which the degree of neutralisation is lowest and in which liquid is received first, to the zone containing conventional superabsorbent material. Exploitation of the absorbent article can be increased and the risk of gel blocking in the sheet or layer closest to the wearer reduced.

A further example is that the partially neutralised superabsorbent is placed in a layer or sheet in the bottom or lower part of the structure, which hereby can work as a liquid dispersion sheet or layer.

The concentration of the partially neutralised superabsorbent material in the aforedescribed examples may be at least 40 percent by weight in those regions in which said partially neutralised superabsorbent material is placed.

However, in the preferred embodiments the partially neutralised superabsorbent material is included with the sole purpose of achieving the decrease in pH desired for ablating the undesired side effects.

Since partially neutralised superabsorbent can be used in high concentrations, the superabsorbent can be used beneficially in a thin absorbent structure. A thin absorbent structure can be obtained with dry formed, compressed chemithermomechanical pulp, CTMP, chemical pulp, CP, or the like. A thin product is of interest because it can be worn discretely and comfortably.

In a preferred embodiment of the invention, the absorbent structure includes dry-formed, compressed CTMP pulp, CP pulp or the like, besides partially neutralised superabsorbent. The absorbent structure is conventionally formed into a mat which is then highly compressed. This results in a very thin absorbent structure. In this case, partially neutralised superabsorbent is mixed in the core. For instance, the superabsorbent may be mixed homogeneously with the cellulose fibres in a so-called mixed layer, or placed between two cellulose-based layers. As with the aforedescribed structure, the amount of neutralised superabsorbent present will correspond to at least 40 percent by weight based on the total weight of the absorbent structure in a dry state in the region or regions in which the superabsorbent material is distributed. The degree of neutralisation is between 20 and 50%, preferably between 25 and 35%.

The use of dry-formed, compressed CTMP pulp, CP pulp or the like in the absorbent structure results in a thin product that can be worn discretely. The undesired side effects, such as malodours and skin irritations are avoided at the same time, as described above. The aforementioned drawbacks in the form of gel blocking and lump formation are also avoided, and a high absorption capacity is achieved.

Characteristic features of the compressed inventive structure are that the core is thin prior to being wetted and swells and disperses liquid instantaneously as it is wetted. The use of dry-formed, compressed paper pulp in the absorbed structure enables the structure to be given a thinness of from 1 to 3 mm. Cores as thin as 0.5 mm can also be obtained and then used in panty liners, for instance. Child diapers need to have a higher absorption capacity, suitable thicknesses in this respect being in the order of up to 8 mm. Preferred thicknesses are from 1 to 8 mm and from 1 to 3 mm respectively.

Wearer comfort is retained in spite of the high concentration of superabsorbent, because the partially neutralised superabsorbent has a slower absorbent rate and a lower absorption capacity.

The invention also relates to absorbent articles, such as diapers, pants diapers, incontinence protectors, sanitary napkins, panty liners and like articles that include an upper liquid-permeable sheet, a lower liquid-impermeable barrier sheet, and an absorbent structure enclosed therebetween, said absorbent structure being of the kind described above.

Absorbent articles also normally include an acquisition/transportation layer between the upper liquid-permeable top sheet and the absorbent structure. An acquisition/transportation layer has an open and airy structure and functions to rapidly accept a given volume of liquid and to rapidly conduct this liquid to the absorbent structure. The acquisition/transportation layer may be comprised of a nonwoven material, which can be produced by through-air bonding and carding or by needling of synthetic fibres, such as polyester, polypropylene or mixtures thereof. The aforedescribed acquisition/transportation layer comprising essentially of synthetic, relatively hydrophobic fibres, are not included in that which relates to the absorbent structure in the present patent application. An absorbent article according to the invention can, on the other hand, include such an acquisition/transportation layer.

According to one preferred embodiment, the article is an incontinence product or a feminine product.

By the word "comprise" as used in this document is meant include although with no limitation.

We claim:

1. An absorbent structure for absorbent articles, the absorbent structure comprising:
    a wetting region comprising partially neutralized superabsorbent material, the partially neutralized superabsorbent material having a degree of neutralization between 25 and 35%;
    and a region outside of the wetting region including a superabsorbent material having a degree of neutralization greater than the neutralization of the partially neutralized superabsorbent material,
    wherein the absorbent structure has a thickness of 1 mm to 8 mm when dry,
    wherein the wetting region comprises at least 40% by weight of the partially neutralized superabsorbent material,
    wherein the partially neutralized superabsorbent material is localized in the crotch area of the article, and
    wherein the superabsorbent material having a degree of neutralization greater than the neutralization of the partially neutralized superabsorbent material is located in the ends of the article.

2. An absorbent structure according to claim 1, wherein the absorbent structure includes dry-formed, compressed chemithermomechanical pulp or chemical pulp.

3. An absorbent structure according to claim 1, wherein said structure has a thickness of 1 mm to 3 mm when dry.

4. An absorbent structure according to claim 1, wherein said absorbent structure is intended for incontinence protectors or feminine products.

5. An absorbent structure according to claim 1, wherein the superabsorbent material having a degree of neutralization greater than the neutralization of the partially neutralized superabsorbent material has a degree of neutralization of about 70%.

6. An absorbent structure according to claim 1, wherein the structure comprises a first zone closer to the wearer including the partially neutralized superabsorbent material and a second zone located beneath the first zone in a direction from the wearer of the absorbent article, wherein the second zone comprises superabsorbent material having a degree of neutralization of about 70%.

7. An absorbent structure according to claim 1, wherein the partially superabsorbent is placed in a layer or sheet in a bottom or lower part of the structure.

8. An absorbent article comprising:
    an upper liquid-permeable sheet,
    a bottom liquid-impermeable barrier sheet, and
    an absorbent structure according to claim 1 enclosed therebetween.

9. An absorbent structure according to claim 1, wherein the absorbent article is a diaper, pants diaper, incontinence protector, sanitary napkin, or panty liner.

10. An absorbent structure according to claim 8, wherein the absorbent article is a diaper, pants diaper, incontinence protector, sanitary napkin, or panty liner.

11. An absorbent structure for absorbent articles, the absorbent structure comprising:
    a first zone arranged closer to a wearer including partially neutralized superabsorbent material, the partially neutralized superabsorbent material having a degree of neutralization between 20% and 50%;
    and a second zone located beneath the first zone in a direction away from the wearer, the second zone including superabsorbent material having a degree of neutralization greater than the degree of neutralization of the partially neutralized superabsorbent material,
    wherein the absorbent structure has a thickness of 1 mm to 8 mm when dry,
    wherein the first zone comprises at least 40% by weight of the partially neutralized superabsorbent material,
    wherein the partially neutralized superabsorbent material is localized in the crotch area of the article, and
    wherein the superabsorbent material having a degree of neutralization greater than the neutralization of the partially neutralized superabsorbent material is located in the ends of the article.

12. The absorbent structure according to claim 11, wherein the superabsorbent material having a degree of neutralization greater than the degree of neutralization of the partially neutralized superabsorbent material has a degree of neutralization of about 70%.

13. An absorbent structure for absorbent articles, the absorbent structure comprising:
    a first zone arranged closer to a wearer including partially neutralized superabsorbent material, the partially neutralized superabsorbent material having a degree of neutralization between 25% and 35%;
    and a second zone located beneath the first zone in a direction away from the wearer, the second zone including superabsorbent material having a degree of neutralization greater than the degree of neutralization of the partially neutralized superabsorbent material,
    wherein the absorbent structure has a thickness of 1 mm to 8 mm when dry,
    wherein the first zone comprises at least 40% by weight of the partially neutralized superabsorbent material,
    wherein the partially neutralized superabsorbent material is localized in the crotch area of the article, and
    wherein the superabsorbent material having a degree of neutralization greater than the neutralization of the partially neutralized superabsorbent material is located in the ends of the article.

* * * * *